(12) United States Patent
Ramsier et al.

(10) Patent No.: US 7,677,082 B2
(45) Date of Patent: Mar. 16, 2010

(54) SOLID STATE GAS SENSORS BASED ON TUNNEL JUNCTION GEOMETRY

(75) Inventors: Rex D. Ramsier, Berlin Center, OH (US); Desmond Lundy, Victoria (CA)

(73) Assignee: The University of Akron, Akron, OH (US)

( * ) Notice: Subject to any disclaimer, the term of this patent is extended or adjusted under 35 U.S.C. 154(b) by 198 days.

(21) Appl. No.: 10/556,650

(22) PCT Filed: May 20, 2003

(86) PCT No.: PCT/US03/15749

§ 371 (c)(1),
(2), (4) Date: Dec. 26, 2006

(87) PCT Pub. No.: WO2004/106908

PCT Pub. Date: Dec. 9, 2004

(65) Prior Publication Data

US 2007/0119234 A1      May 31, 2007

(51) Int. Cl.
*G01N 27/02*      (2006.01)
(52) U.S. Cl. .................................................. 73/31.05
(58) Field of Classification Search .................. 73/31.05
See application file for complete search history.

(56) References Cited

U.S. PATENT DOCUMENTS

| | | | |
|---|---|---|---|
| 4,007,096 A | 2/1977 | Jasinski et al. | |
| 4,514,263 A | 4/1985 | Janata | |
| 4,569,918 A | 2/1986 | Moore et al. | |
| 4,671,852 A | 6/1987 | Pyke | |
| 4,718,991 A | 1/1988 | Yamazoe et al. | |
| 4,855,034 A | 8/1989 | Sugimoto et al. | |
| 4,978,434 A | 12/1990 | Jones et al. | |
| 4,996,073 A | 2/1991 | Copeland et al. | |
| 5,041,204 A | 8/1991 | Kuhn et al. | |
| 5,128,018 A | 7/1992 | Kiesele | |
| 5,372,785 A | 12/1994 | Johnson et al. | |
| 5,716,506 A | 2/1998 | Maclay et al. | |
| 5,800,630 A | 9/1998 | Vilela et al. | |
| 5,841,021 A | 11/1998 | DeCastro et al. | |
| 6,165,336 A | 12/2000 | Maki et al. | |
| 6,179,992 B1 | 1/2001 | Nafe et al. | |
| 6,200,445 B1 | 3/2001 | Yokota et al. | |
| 6,290,838 B1 | 9/2001 | Mifsud et al. | |
| 6,298,710 B1 | 10/2001 | Samman et al. | |
| 6,368,479 B1 | 4/2002 | Yokota et al. | |
| 6,503,831 B2 | 1/2003 | Speakman | |
| 2002/0017126 A1 | 2/2002 | DiMeo, Jr. et al. | |
| 2002/0108856 A1* | 8/2002 | Kunimoto et al. | ........... 204/425 |

* cited by examiner

*Primary Examiner*—Daniel S Larkin
(74) *Attorney, Agent, or Firm*—Roetzel & Andress; Joseph J. Crimaldi

(57) ABSTRACT

A gas detector utilizing tunnel junction geometry is disclosed. The gas detector comprises a first electrically conductive material layer, an electrically nonconductive material layer disposed on the first electrically conductive material layer, a second electrically conductive material layer disposed on the electrically nonconductive material layer, a gas source (34) in fluid communication with the second electrically conductive material layer; and a power source in electrical communication with the first and second electrically conductive material layers. A method of detecting a gas utilizing the detector of the present invention is also disclosed. A method of making a gas detector is likewise disclosed.

26 Claims, 2 Drawing Sheets

SOLID STATE GAS SENSORS BASED ON TUNNEL JUNCTION GEOMETRY

BACKGROUND OF THE INVENTION

This invention relates to solid state gas sensors. More particularly, this invention relates to solid state gas sensors for sulfur dioxide. Even more particularly, this invention relates to solid state sulfur dioxide sensors using Al—$Al_2O_3$—Au structures.

Sulfur dioxide ($SO_2$) is a gas that is both useful in industrial applications and an undesired byproduct of some processes. For example, $SO_2$ is used to produce cooking liquors for paper making, but it is also considered a pollutant from lime kilns. Government mandates limit the amount of $SO_2$ that may be emitted from the paper making process.

$SO_2$ is also a useful compound in the wine making industry, where it is used to delay bacterial growth. However, it also is a byproduct of yeast fermentation and $SO_2$ levels in wine can vary with temperature and pH. This variation may adversely affect the quality of the final product. Therefore, effective monitoring and control of $SO_2$ levels is generally recognized as essential to all phases of wine making. The standard methods of monitoring $SO_2$ have been the Ripper or iodine method and the vacuum aspiration method. Both of these methods are unsuitable for testing on location, requiring that samples be taken from a cellar to a laboratory for analysis. This may cause a significant delay before corrective dosing, if necessary, can be effected.

The Ripper method is also susceptible to several sources of error. Phenolic substances in red wines, for example, react with the reagent iodine to produce results that indicate a higher level of $SO_2$ than is actually present. The end point of this test is also not well defined and the results tend to fade quickly. The Ripper method is also susceptible to skewing by ascorbic acid. Additionally, juice from grapes affected by botrytis cannot be accurately measured by iodine titration. Furthermore the iodine reagent is unstable and must be standardized by titration with sodium thiosulphate periodically. Iodine reagent is also extremely sensitive to sunlight.

$SO_2$ plays a role in many other industries as well. For example, the ability to minimize emissions of $SO_2$ from aircraft may also have an impact on the ability of the aerospace industry to develop new supersonic transport vehicles. Furthermore, $SO_2$ is corrosive of some combustion engine components. $SO_2$ has also been shown to play a role in fouling catalysts used in the automotive and petroleum industries. $SO_2$ is also generated during the regeneration of sorbents for coal gasification. Therefore, there is a need to monitor $SO_2$ levels in a wide variety of industries, where a lack of appropriate chemical sensors can be a limiting factor for many technologies. This is especially true in the case of sulfur dioxide ($SO_2$) monitoring.

Recent efforts in the area of gas detection incorporate solid electrolytes, metal oxides, or polymer coatings as the detectors' active region. Gas detectors utilizing solid electrolytes are disclosed in a number of U.S. patents. For example, U.S. Pat. No. 4,855,034 discloses a sulfur dioxide sensor which utilizes a solid electrolyte of a compound of sodium oxide and aluminum oxide (β-alumina). The sensor also includes a platinum, lead, or platinum-lead alloy which accelerates the reaction of sulfur dioxide with oxygen.

U.S. Pat. No. 6,179,992 discloses a gas detection systems that contains an oxygen ion conducting solid electrolyte and a metallic salt which acts as a gas sensitive layer. A cationically conductive material is disposed between the electrolyte and the gas sensitive material. U.S. Pat. No. 6,200,445 also discloses a sulfur dioxide sensor that comprises a solid electrolyte that has oxygen ion conductivity. A detecting electrode is electrically connected to at least part of the surface of the solid electrolyte, and a basic electrode is also connected to at least a part of the surface of the solid electrolyte. The detecting electrode contains glass and either gold or a gold alloy. The basic electrode contains platinum or a platinum alloy. The glass component of the detecting electrode is reported to suppress reaction of inflammable gases such as carbon monoxide. A similar sensor is also disclosed in U.S. Pat. No. 6,368,479.

U.S. Pat. No. 4,718,991 discloses a "proton conductor gas sensor" for detecting gases, such as sulfur dioxide, which produce protons upon reacting with water. The gas sensor comprises a proton conductor which may be antimonic acid, zirconium phosphate, dodecamolybdophosphoric acid and the like. Attached to the proton conductor is an ionization electrode and a reference electrode. The ionization and reference electrodes may be platinum, rhodium or other metals. Silver and gold are also listed as potential materials for the reference electrode.

The use of metal oxides in gas sensors is also known. For example, the use of a zirconium oxide probe to measure sulfur dioxide levels in a combustion system is disclosed in U.S. Pat. No. 4,978,434.

A system utilizing thin film electrodes coated with an electrolyte film is disclosed in U.S. Pat. No. 5,716,506. The thin film electrodes may be platinum and the electrolyte film is capable of conducting electricity at room temperature. The sensor comprises a substrate which may be silicon dioxide, alumina, or a polymer, a working electrode deposited on the substrate, a counter electrode also deposited on the substrate and a film of polymer electrolyte applied over both electrodes. The working electrode comprises a first layer of gold, platinum or carbon which is in contact with the substrate and a second layer of platinum in contact with the first layer. The first layer has a thickness of about 250 to about 5000 angstroms.

Other types of sensors for the selective detection of gases are also known. U.S. Pat. No. 5,841,021, discloses an electrochemical gas sensor for detecting a variety of gases including oxides of sulfur. The sensor has an electrode which reacts to the presence of the gas in question, a reference electrode which does not react to the gas in question, and an electrically conducting substrate which connects the two electrodes. A gas sensor is disclosed in U.S. Pat. No. 6,165,336 which utilizes a gas permeation element which allows the separation of a gas of interest such as carbon monoxide from gases that may cause deterioration of the sensor. U.S. Pat. No. 5,041,204 is directed to an electrochemical method for detecting sulfur dioxide or hydrogen cyanide using copper ions. U.S. Pat. No. 5,128,018 is also an electrochemical apparatus for detecting gases such as sulfur dioxide. This system makes use of heteropoly acids or iron salts in an electrolyte in an electrochemical measuring cell. U.S. Pat. No. 5,041,204 discloses a electrochemical measuring cell for detecting hydrogen cyanide or sulfur dioxide using a pair of electrodes disposed in an electrolyte.

The adsorption of $SO_2$ onto clean metal surfaces is known. For example, it is known that room temperature adsorption of $SO_2$ on copper surfaces is dissociative, forming adsorbed S(a), O(a), and SO(a) species. However, a method for using gas adsorption onto metal surfaces in connection with tunnel junction geometry for devices has not been known.

Therefore, there is a continuing need for alternate methods of detecting gases such as $SO_2$. There is also a need for a gas sensor, especially a sensor for $SO_2$, that is portable and easy to use. There is a continuing need for detectors that are smaller, lighter in weight, and require less power than present day detection schemes. There is a particular need for $SO_2$ detectors in the wine industry that provide results with a minimum of delay from the time of taking a sample, and that are easy to use.

BRIEF SUMMARY OF THE INVENTION

It is, therefore, an aspect of the present invention to provide a gas sensor for sulfur dioxide that is portable and inexpensive.

It is another aspect of the present invention to provide a gas sensor that relies on tunnel junction geometry to detect $SO_2$.

It is still another aspect of the present invention to provide a method for detecting a gas, where the sensor utilizes tunnel junction geometry to detect a particular gas or groups of gases.

At least one or more of the foregoing aspects, together with the advantages thereof over the known art relating to gas detection, which shall become apparent from the specification which follows, are accomplished by the invention as herein after described and claimed.

In general, the present invention provides a gas detector comprising a first electrically conductive material layer, an electrically nonconductive material layer disposed on the first electrically conductive material layer; a second electrically conductive material layer disposed on the electrically nonconductive material layer; a gas source in fluid communication with the second electrically conductive material layer; and a power source in electrical communication with the first and second electrically conductive material layers.

The present invention also provides a method of detecting a gas, the method comprising determining the change in impedance of a tunnel junction device upon exposure to a gas sample, wherein the tunnel junction device contains a first electrically conductive material layer, an electrically nonconductive material layer disposed on the first electrically conductive material layer, and a second electrically conductive material layer disposed on the electrically nonconductive material layer, and wherein the first and second electrically conducting layers are in electrical communication with a power source.

A method of making a gas detector is also provided. The method comprises forming a first electrically conductive material layer, disposing an electrically nonconductive material layer on the first electrically conductive material layer, disposing a second electrically conductive material layer on the electrically nonconductive material layer, and placing the first and second electrically conducting layers in electrical communication with a power source.

DETAILED DESCRIPTION OF THE INVENTION

Figure 1:
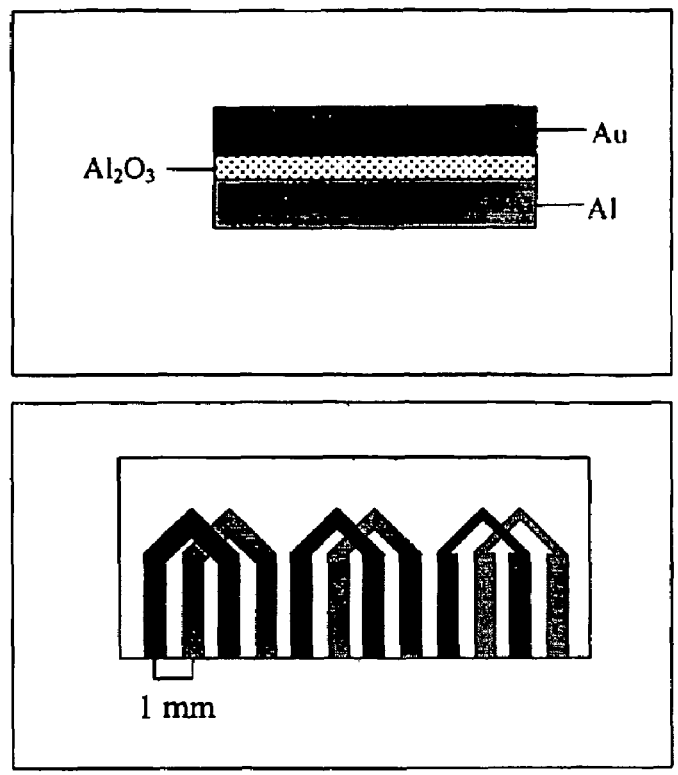
FIG. 1 is a schematic representation of the active surface of the gas sensor of the present invention.

The present invention is a gas sensor based on high vacuum evaporated metal-insulator-metal tunnel junctions and an associated method of testing for a gas. The sensor comprises an electrically conductive material layer, such as a metal or a metal alloy, as a first layer. An electrically nonconductive material layer is disposed on the first electrically conductive material layer and a second electrically conductive material layer, such as a metal or metal alloy, is disposed on the electrically nonconductive material layer, forming a tunnel junction apparatus.

The first electrically conductive material layer may contain a metal or a metal alloy. Preferred metals include alkaline earth metals such as magnesium, transition metals such as chromium, titanium and zirconium, and other metals such as aluminum, and their alloys. Aluminum and aluminum alloys are particularly preferred due to their relatively low cost, low density, and ease of handling. The first conductive layer may be any thickness, provided that a uniform, solid layer is provided. However, because it is desirable to minimize the weight of the detector, the layer may preferably be between about 100 nm and about 500 nm thick. In one example, the first layer of conductive material is at least about 200 nm thick.

The electrically nonconductive or insulating layer is a sufficiently thin layer so that it acts as an insulator, yet electrons are capable of migrating through the material to form a tunnel junction device. In one example, the nonconducting layer is between about 2 and about 10 nm thick. Preferred materials for the nonconducting layer include aluminum oxide, magnesium oxide, chromic oxide, titanium dioxide, zirconium oxide, silicon dioxide, and the like.

The second electrically conductive material layer is disposed on the electrically nonconductive material layer and preferably is selectively catalytic for the gas to be detected. The second electrically conductive material layer may also have a strong affinity for at least one catalytic product. For example, gold selectively catalyzes $SO_2$ dissociation and is permanently contaminated by sulfur after less reactive species are removed. Other noble metals such as silver, platinum, rhodium, iridium, palladium, ruthenium, and osmium may also be used, depending on the gas to be detected. It is also envisioned that alloys and solid solutions of noble metals may also be used such as platinum-iridium, palladium-gold, platinum-silver and palladium-gold. The second conductive layer may be any thickness, provided that a uniform, solid layer is provided. However, because it is desirable to minimize the weight and cost of the detector, the layer may preferably be between about 100 and about 500 nm thick. In one example, the second layer of conductive material is at least about 200 nm thick. In one particular example, the second layer of conductive material has a thickness of about 250 nm.

The first and second electrically conductive materials are placed in electrical communication with a power source to measure the change in impedance upon exposure to the sample. In one example, the power source is a direct current (DC) power source. In another example the power source is an alternating current (AC) power source. In still another example, both a direct current and an alternating current power source are placed in electrical communication with the conducting layers. The power source preferably provides electrical current below a level which will cause the device to heat and eventually short out. In one example, the current is no greater than 10 milliamperes (mA).

In order to demonstrate the practice of the current invention, $SO_2$ detectors according to the present invention were synthesized. The following examples should not be viewed as limiting the scope of the invention. The claims will serve to define the inventions. Testing was performed in a high vacuum test stand. It is anticipated that devices according to the present invention will be used in environments other than vacuum. The devices were tested under vacuum to minimize surface contamination, such as that resulting from the adsorption of volatile hydrocarbons and water vapor from the laboratory air. In these examples, both the AC and DC response of the devices using a simple modular design and circuitry was measured.

The sensing device of the present invention was fabricated in a diffusion-pumped bell jar system with a base pressure of $10^{-8}$ torr. Glass microscope slides are cut to fit a substrate holder mounted inside the vacuum system, and then cleaned by sonication and rinsing with solvents (reagent grade acetone and isopropyl alcohol). The patterned geometry of the test devices as shown in FIG. 1 is transferred to the glass substrates by thermal evaporation through arc-machined stainless steel masks. In the present case, Al (99.999% pure) is evaporated at pressures in the $10^{-7}$ torr range to a thickness greater than 200 nm to form the base electrode. A thin film of insulating alumina is then grown on the surface of the Al electrode by exposure to a DC oxygen glow discharge (nominally 100 mtorr, 550 V, 275 mA) for approximately 30 minutes. The sample stage is then rotated to place the substrate over a second evaporation station, where Au (99.999% pure) cover electrodes are evaporated. The thickness of the gold films can be measured by a quartz crystal thickness monitor and is approximately 250 nm for the data presented here.

After the evaporation and oxidation steps are complete, the vacuum system is vented with dry nitrogen and the samples transferred to the test stand for electrical measurements. However, the relative humidity when we open the chamber affects the composition of the background gas present when the next sample is fabricated, and differences in the hydroxyl content of the alumina films will manifest themselves as scatter in our data. Note in FIG. 1 that each evaporation sequence produces three independent tunnel junctions, each with a different cross sectional area. The data presented herein demonstrate that these geometric factors do not play a role in the sensing capabilities of the structures, and therefore, that this concept of using tunnel junctions as gas sensors is transferable to other fabrication technologies and geometries. Note also that the spacing of the leads is matched to that of a RS Components printed circuit board edge connector (#466-539) so that the devices plug directly into the connector. This circumvents making electrical connections to the samples by hand and facilitates the transfer process between vacuum systems.

Figure 2A:
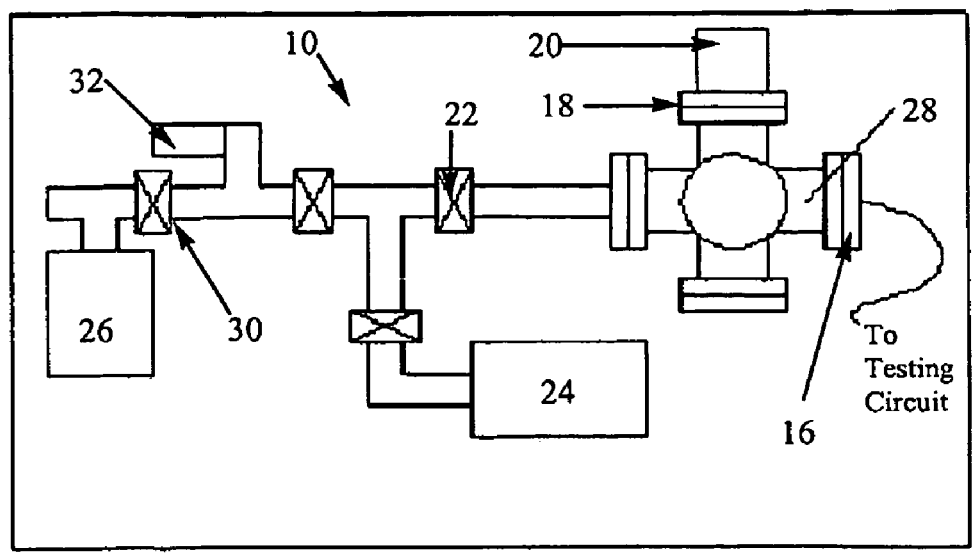
FIG. 2a is a schematic representation of a high vacuum test apparatus taken from a side view.
Figure 2B:
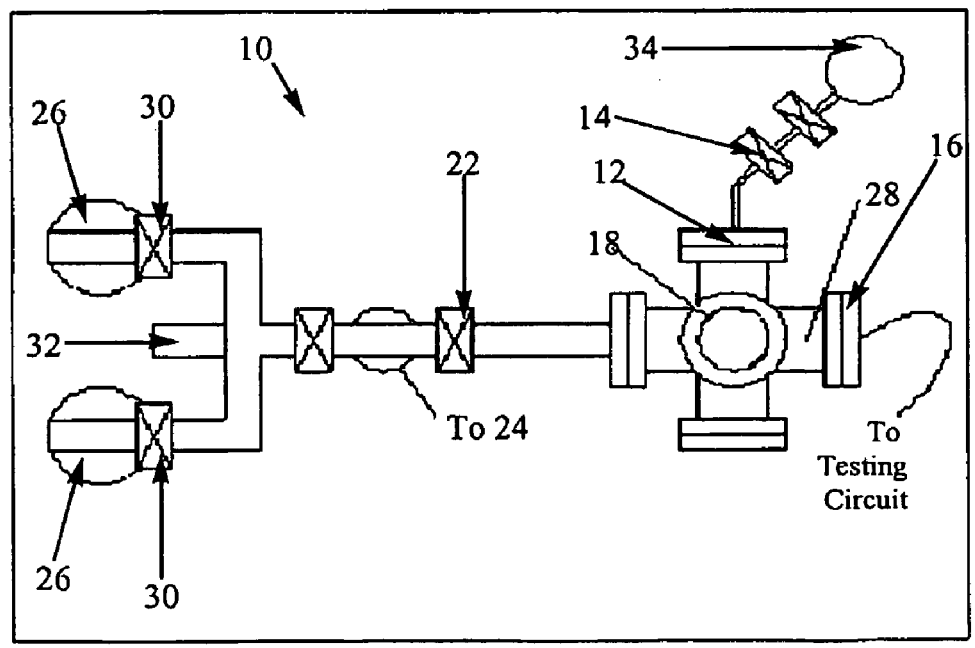
FIG. 2b is a schematic representation of a high vacuum test apparatus taken from a top view.

As illustrated in FIG. 2, we have constructed a sorption-pumped high vacuum system specifically for testing these gas sensors. The test stand (10) is an all stainless steel system with copper-gasket sealed fittings and bakeable valves. The testing chamber (28) is a six-way cross which accepts 4.5 inch OD Conflat flanges, and is large enough to accommodate the detectors while also enclosing the smallest volume possible to limit the amount of $SO_2$ gas used. One of the ports (12) on the chamber allows for gas entry through a bellows valve (14). Another port (16) provides for sample mounting in the edge connector. Another port (18) is for pressure measurement in the $10^{-2}$-$10^{-7}$ torr range with a capacitance manometer (Baratron) (20), and another port leads through a gate valve (22) to the pumps.

The chamber (28) is pumped by a mechanical roughing pump (24) in parallel with two sorption pumps (26). In normal operation, the device to be tested is plugged into the edge connector and the flange is then mounted on the test chamber using a new copper gasket. The sorption pumps (26) are isolated by right angle bellows valves (30) and cooled with liquid nitrogen while the roughing pump (24) is used to bring the system to approximately $10^{-2}$ torr as measured by a Pirani gauge (32). The mechanical pump (24) is then isolated and shut off and the sorption pumps (26) bring the test chamber to the $10^{-8}$ torr range where the manometer is zeroed. This procedure provides a hydrocarbon-free environment void of mechanical or electrical noise in which the devices are tested.

Testing is performed by leaking $SO_2$ into the chamber and then removing it by pumping with the sorption pumps. The corrosive gas is trapped by the large surface area molecular sieve within the cooled pumps so there is no exhaust and testing can be performed without a fume hood or exhaust-gas handling system. A null bridge with decade resistors and capacitors was used for monitoring changes in the electrical response of the devices due to exposure to $SO_2$. A voltage divider was used to limit the total current, as currents above the 10 mA range in this apparatus cause heating and eventual shorting out of the devices. These small currents in turn yield small voltage drops across the junctions which add to scatter in the resulting data. A multipole switch was used to rotate the measurements between the three junctions during testing. Steady state results reflecting net changes in the electrical properties of the devices due to integrated exposure to $SO_2$ gas are reported.

Figure 3:
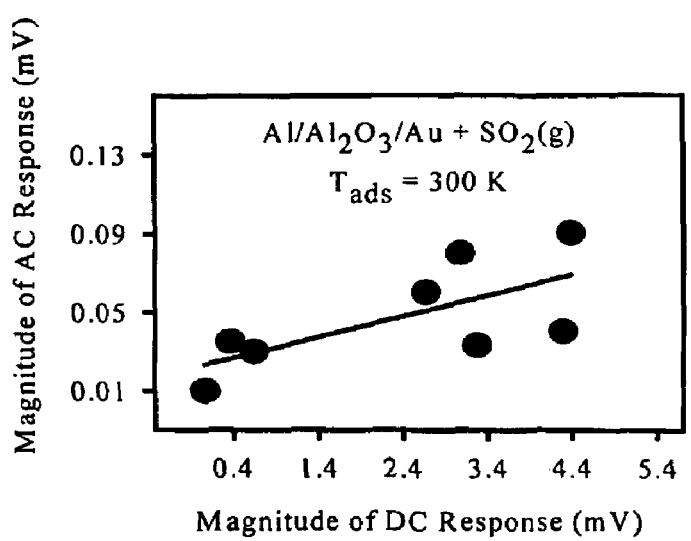
FIG. 3 is graph showing the magnitude of AC response versus the magnitude of DC response for gas sensors according to the present invention.

FIG. 3 presents data following adsorption of $SO_2$ onto the gold surfaces of the tunnel junctions at room temperature (approximately 300 K). The $SO_2$ exposure and glow discharge times for each of these eight samples are essentially the same, but they are fabricated over about a one month time frame. The data from three junctions on each sample are averaged in FIG. 3 (unless a junction is shorted) since the electrical response presented in this manner is independent of the cross sectional area of the junctions as discussed below. The data cluster around a linear trend line. If all the fabrication conditions were exactly the same for all samples, the data of FIG. 3 (collected at fixed frequency) would be expected to lie at the same coordinates. However, humidity variations in the growth chamber influence the hydroxyl content and thus the conductivity and permittivity of the oxide layers. The data in FIG. 3 shows that these electrical properties vary proportionally to one another as discussed more fully below.

The data indicate that the devices respond to $SO_2$ exposure pressures in the $10^{-2}$ torr range. Ideally, a gas detector will respond only to $SO_2$ and not to other gases. This would imply that at atmospheric pressures on the order of $10^3$ torr these detectors would respond to $SO_2$ concentrations of about one part in $10^5$. This level of detection demonstrates that a tunnel junction geometry for devices will operate as gas sensors for $SO_2$.

There is a simple way to understand why the data of FIG. 3 should follow a linear trend and be independent of the cross sectional area of the junctions if one considers the junction region as a leaky parallel plate capacitor and neglects the impedance of the connecting leads. The AC voltage response is proportional to the inverse of the capacitance of the junction, $$V_{AC} \propto \frac{d}{\varepsilon A} \quad (1)$$

where d and A are the thickness and cross-sectional area of the insulator layer forming the junction, respectively and $\varepsilon$ is its effective dielectric constant. The DC voltage response of the junction also involves its geometric properties and its electrical conductivity, $\sigma$, $$V_{DC} \propto \frac{d}{\sigma A} \quad (2)$$

so that the ratio of the two voltages which represents the slope of the line shown in FIG. 3 is $$\frac{V_{AC}}{V_{DC}} \propto \frac{\sigma}{\varepsilon}. \quad (3)$$

This ratio is constant at fixed frequency ($\omega$) assuming a standard model such as $$\varepsilon(\omega) = \varepsilon^\circ(\omega) + 4\pi i \frac{\sigma(\omega)}{\omega} \quad (4)$$

where we interpret $\varepsilon(\omega) - \varepsilon^\circ(\omega)$ as the effective dielectric constant $\varepsilon$ in Eq. (3). This demonstrates why $\varepsilon$ and $\sigma$ should vary proportional to one another as the hydroxyl content of the oxide layers varies from sample to sample, and thus why we expect the data of FIG. 3 to cluster around a linear trend line.

As mentioned above, the adsorption of $SO_2$ onto clean metal surfaces, such as gold, is known. Sulfur is also a known natural contaminant of gold. In the present apparatus, the gold surface acts to catalyze $SO_2$ dissociation and is permanently contaminated (poisoned) by sulfur after the weakly bound species are pumped away. The process of chemisorption involves electron transfer and redistribution processes which alter the DC and AC impedance of the devices and thus the voltages measured across the tunnel junction.

This effect is distinctly different from other gas sensor designs that use gold electrodes (such as those for $NO_2$) since in that case there is no dissociation and thus no permanent modification of the structures. In the present invention, the ability to reuse the device is conceded, but given the simplicity and low fabrication cost of the present invention, this is an acceptable trade-off. It is believed that the present invention will also work for other sulfur containing compounds that dissociate on gold. However, the gas detector of the present invention should not be influenced by reactions with common atmospheric gases such as oxygen and carbon dioxide since these do not dissociate on gold surfaces. In summary, we have shown that a tunnel junction configuration can be used as the basis for a detector of integrated $SO_2$ exposure.

Based upon the foregoing disclosure, it should now be apparent that gas detectors utilizing tunnel junction geometry will carry out the objects set forth hereinabove. It is, therefore, to be understood that any variations evident fall within the scope of the claimed invention and thus, the selection of specific component elements can be determined without departing from the spirit of the invention herein disclosed and described.

We claim:

1. A gas detector comprising:
   a first electrically conductive material layer;
   an electrically nonconductive material layer disposed on the first electrically conductive material layer;
   a second electrically conductive material layer disposed on the electrically nonconductive material layer;
   a gas source in fluid communication with the second electrically conductive material layer; and
   a power source in electrical communication with the first and second electrically conductive material layers,
   wherein the first electrically conductive material layer is formed from an electrically conductive material that is non-catalytic for the gas to be detected, wherein the second electrically conductive material layer is formed from an electrically conductive material that is selectively catalytic for the gas to be detected, and wherein the first electrically conductive material layer contains a metal selected from the group consisting of aluminum, magnesium, chromium, titanium and zirconium.

2. The gas detector according to claim 1, wherein the second electrically conductive material layer contains a metal selected from the group consisting of silver, gold, platinum, rhodium, iridium, palladium, ruthenium, and osmium.

3. The gas detector according to claim 2, wherein the second electrically conductive material layer contains gold.

4. The gas detector according to claim 1, wherein the electrically nonconductive material layer contains at least one compound selected from the group consisting of aluminum oxide, magnesium oxide, chromic oxide, titanium dioxide, zirconium oxide, and silicon dioxide.

5. The gas detector according to claim 1, wherein the power source is a direct current power source.

6. The gas detector according to claim 1, wherein the power source is an alternating current power source.

7. A gas detector comprising:
   a first electrically conductive material layer;
   an electrically nonconductive material layer disposed on the first electrically conductive material layer;
   a second electrically conductive material layer disposed on the electrically nonconductive material layer;
   a gas source in fluid communication with the second electrically conductive material layer; and
   a power source in electrical communication with the first and second electrically conductive material layers,
   wherein the first electrically conductive material layer is formed from an electrically conductive material that is non-catalytic for the gas to be detected, wherein the second electrically conductive material layer is formed from an electrically conductive material that is selectively catalytic for the gas to be detected, and wherein the gas detector is capable of detecting sulfur dioxide.

8. The gas detector according to claim 7, wherein the first electrically conductive material layer contains a metal selected from the group consisting of aluminum, magnesium, chromium, titanium and zirconium.

9. The gas detector according to claim 7, wherein the second electrically conductive material layer contains a metal selected from the group consisting of silver, gold, platinum, rhodium, iridium, palladium, ruthenium, and osmium.

10. The gas detector according to claim 9, wherein the second electrically conductive material layer contains gold.

11. The gas detector according to claim 7, wherein the electrically nonconductive material layer contains at least one compound selected from the group consisting of aluminum oxide, magnesium oxide, chromic oxide, titanium dioxide, zirconium oxide, and silicon dioxide.

12. The gas detector according to claim 7, wherein the power source is a direct current power source.

13. The gas detector according to claim 7, wherein the power source is an alternating current power source.

14. A method of determining the presence of a gas, the method comprising determining the change in impedance of a tunnel junction device upon exposure to a gas sample, wherein the tunnel junction device comprises:
  a first electrically conductive material layer;
  an electrically nonconductive material layer disposed on the first electrically conductive material layer; and
  a second electrically conductive material layer disposed on the electrically nonconductive material layer,
  wherein the first and second electrically conducting layers are in electrical communication with a power source, wherein the first electrically conductive material layer is formed from an electrically conductive material that is non-catalytic for the gas to be detected, and wherein the second electrically conductive material layer is formed from an electrically conductive material that is selectively catalytic for the gas to be detected.

15. The method according to claim 14, wherein the gas to be detected is sulfur dioxide.

16. The method according to claim 15, wherein the gas is obtained from wine.

17. The method according to claim 14, wherein the first electrically conductive material layer contains a metal selected from the group consisting of aluminum, magnesium, chromium, titanium and zirconium.

18. The method according to claim 14, wherein the second electrically conductive material layer contains a metal selected from the group consisting of silver, gold, platinum, rhodium, iridium, palladium, ruthenium, and osmium.

19. The method according to claim 18, wherein the second electrically conductive material layer contains gold.

20. The method according to claim 14, wherein the power source is a direct current power source.

21. The method according to claim 14, wherein the power source is an alternating current power source.

22. The method according to claim 14, wherein the first and second electrically conducting layers are placed in electrical communication with a direct current power source and an alternating current power source and wherein the direct current and alternating current impedances are measured before and after exposure of the second conducting material layer to the sample.

23. A method of making a gas detector comprising:
  forming a first electrically conductive material layer;
  disposing an electrically nonconductive material layer on the first electrically conductive material layer;
  disposing a second electrically conductive material layer on the electrically nonconductive material layer; and
  placing the first and second electrically conducting layers in electrical communication with a power source,
  wherein the first electrically conductive material layer is formed from an electrically conductive material that is non-catalytic for a gas to be detected, wherein the second electrically conductive material layer is formed from an electrically conductive material that is selectively catalytic for a gas to be detected, and wherein the first electrically conductive material layer contains a metal selected from the group consisting of aluminum, magnesium, chromium, titanium and zirconium.

24. The method of claim 23, wherein the second electrically conductive layer is selected from the group consisting of silver, gold, platinum, rhodium, iridium, palladium, ruthenium, and osmium.

25. A method of making a gas detector comprising:
  forming a first electrically conductive material layer;
  disposing an electrically nonconductive material layer on the first electrically conductive material layer;
  disposing a second electrically conductive material layer on the electrically nonconductive material layer; and
  placing the first and second electrically conducting layers in electrical communication with a power source,
  wherein the first electrically conductive material layer is formed from an electrically conductive material that is non-catalytic for a gas to be detected, wherein the second electrically conductive material layer is formed from an electrically conductive material that is selectively catalytic for a gas to be detected, and wherein the gas detector is capable of detecting sulfur dioxide.

26. The method of claim 25, wherein the second electrically conductive layer is selected from the group consisting of silver, gold, platinum, rhodium, iridium, palladium, ruthenium, and osmium.

* * * * *